US00PP19501P2

(12) United States Plant Patent
Kawashima et al.

(10) Patent No.: US PP19,501 P2
(45) Date of Patent: Nov. 25, 2008

(54) **NEW GUINEA *IMPATIENS* PLANT NAMED 'SAKIMP006'**

(50) Latin Name: *Impatiens×hybrida*
Varietal Denomination: SAKIP006

(75) Inventors: Moriya Kawashima, Nagano (JP); Yoneo Kobayashi, Shizuoka (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 11/895,983

(22) Filed: Aug. 28, 2007

(51) Int. Cl.
*A01H 5/00* (2006.01)

(52) U.S. Cl. ..... Plt./318.6

(58) Field of Classification Search ..... Plt./318.6
See application file for complete search history.

*Primary Examiner*—Kent L. Bell
*Assistant Examiner*—June Hwu
(74) *Attorney, Agent, or Firm*—Jondle & Associates P.C.

(57) ABSTRACT

A New Guinea *Impatiens* cultivar particularly distinguished by having large lavender flowers, a mounding plant habit, and vigorous rooting is disclosed.

1 Drawing Sheet

Genus and species: *Impatiens×hybrida.*
Variety denomination: 'SAKIMP006'.

BACKGROUND OF THE NEW PLANT

The present invention comprises a new and distinct cultivar of New Guinea *Impatiens,* botanically known as *Impatiens×hybrida,* and hereinafter referred to the cultivar name 'SAKIMP006'. 'SAKIMP006' originated from an interspecific hybridization between 'NG-02WM1', an unpatented proprietary deep orange-flowered *Impatiens* plant and 'NG-01H-9A', an unpatented proprietary red-orange flowered *Impatiens* plant, in Misato, Japan.

In April 2002, the female parent line 'NG-02WM1' and male parent line 'NG-01H-9A' were crossed and population of $F_1$ plants was created. The $F_1$ plants were evaluated in Misato, Japan in an open field trial. The criteria for plant selection included vigorous rooting, lavender flower color and large flower petal size. At the completion of the trial, one single-plant selection was made based on the above criteria and vegetatively propagated. From May to August 2004, the selection was evaluated in an open field in Misato, Japan. The selection was also evaluated in an open field trial during the summer of 2004 in Athens, Ga., USA. Shoot-tip cuttings of the variety were then shipped to Salinas, Calif., where the plants were regenerated and reevaluated for stability of traits. The selection subsequently was named 'SAKIMP006' and found to have its unique characteristics reproduce true to type in successive generations of asexual propagation. The instant plant was asexual reproduced by vegetative cutting in Salinas, Calif.

Plant Breeder's Rights for this cultivar were applied for in Canada on Mar. 28, 2007.

SUMMARY OF THE INVENTION

The following are the most outstanding and distinguishing characteristics of this new cultivar when grown under normal horticultural practices in Salinas, Calif.

1. Lavender flowers;
2. Large flower petal size;

3. Mounding plant habit; and
4. Vigorous rooting.

DESCRIPTION OF PHOTOGRAPHS

This new *Impatiens* plant is illustrated by the accompanying photographs which show overall plant habit including blooms, buds, and foliage of the plant; the colors shown are as true as can be reasonably obtained by conventional photographic procedures.

Figure 1:
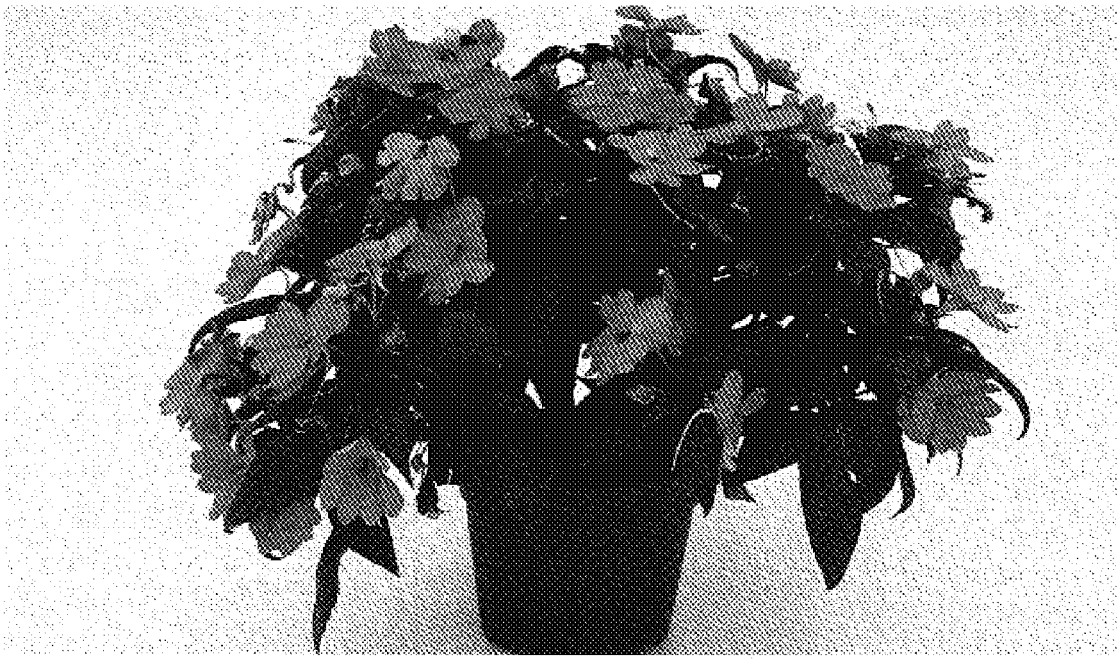

FIG. 1 The photograph shows overall plant habit including blooms, buds and foliage.

Figure 2:
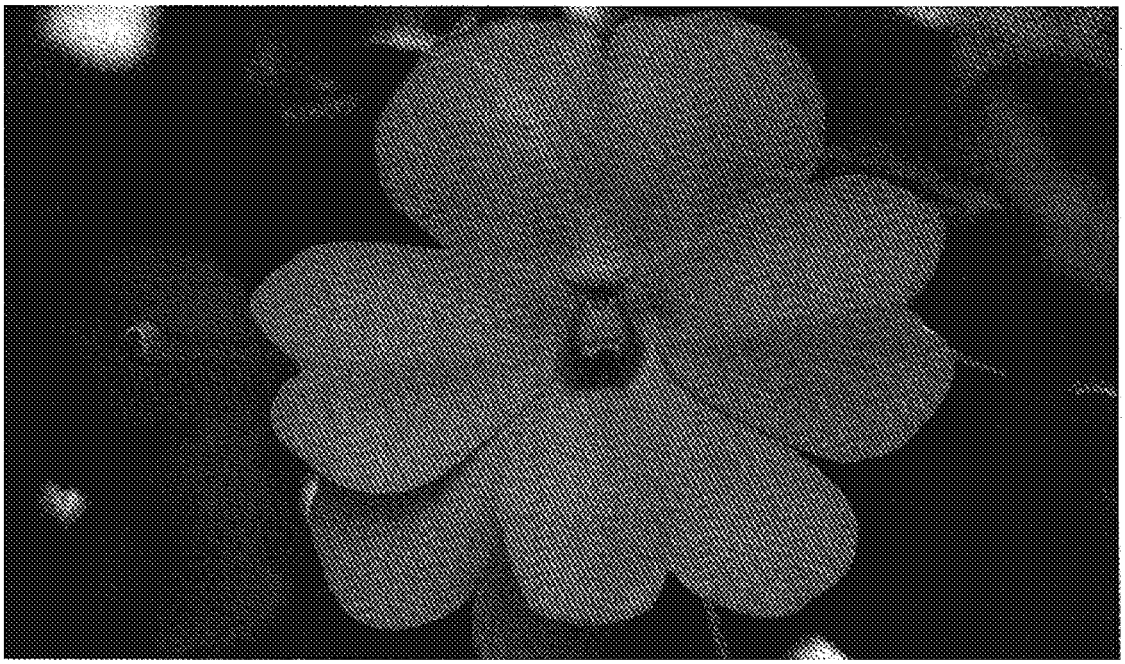

FIG. 2 The photograph shows the mature inflorescence.

DETAILED DESCRIPTION OF THE NEW CULTIVAR

The following detailed descriptions set forth the distinctive characteristics of 'SAKIMP006'. The data which define these characteristics were collected from asexual reproductions carried out in Salinas, Calif. The plant history was taken on plants grown for about four months from propagation by terminal cuttings under greenhouse conditions. Color references are primarily to the R.H.S. Colour Chart of The Royal Horticultural Society of London, (R.H.S.), $4^{th}$ edition (2001). Anatomic labels are from The Cambridge Illustrated Glossary of Botanical Terms, by M. Hickey and C. King, Cambridge University Press.

DETAILED BOTANICAL DESCRIPTION

Classification:
*Family.*—Balsaminaceae.
*Botanical.*—*Impatiens×hybrida.*
*Common name.*—Impatiens.

Parentage:
*Female parent.*—'NG-02WM1', an unpatented proprietary deep-orange flowered *Impatiens* plant.
*Male parent.*—'NG-01H-9A', an unpatented proprietary red-orange flowered *Impatiens* plant.

Growth:

*Time to produce a rooted cutting.*—The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed.

*Environmental conditions for plant growth.*—Rooted cuttings were transplanted and grown in 6-inch plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Plants were fertilized every 2–3 days, 2 times in consecutive applications and then given one clear water application. Pots were top-dressed with a dry, slow release fertilizer containing 14% nitrogen, 14% phosphorus and 14% potassium. The typical average air temperature was 24° C.

*Time to bloom from propagation.*—6 to 8 weeks.

Plant description:

*Habit.*—Mounding.

*Height.*—28.0 cm to 30.0 cm from soil line to top of foliage.

*Spread.*—48.0 cm to 50.0 cm.

*Time to produce a finished flowering plant.*—6 to 8 weeks.

*Time to produce a rooted cutting.*—4 weeks.

*Flowering requirements.*—Will flower so long as temperature is above 5° C.

*Temperature tolerance.*—Plants have been observed to continuously flower at a temperature range of 5° C.–36° C.

Branches:

*Number.*—12 total with 4 main branches.

*Length.*—6.0 cm from soil line to first node: 20.0 cm to 25.0 cm total.

*Diameter* (*main branch*).—2.0 cm.

*Color.*—RHS 187B (Greyed-Purple).

Stems:

*Length.*—7.0 cm from first to second node.

*Diameter.*—0.8 cm to 1.0 cm.

*Internode length.*—5.0 cm to 7.0 cm.

*Color.*—RHS 187B (Greyed-Purple).

*Stem description.*—Strong; circular cross-section, smooth and shiny.

*Pubescence.*—Absent.

*Anthocyanin color.*—RHS 185B (Greyed-Purple).

*Peduncles.*—Length: 4.0 cm. Diameter: 0.2 cm. Color: RHS 185D (Greyed-purple). Texture: Smooth, glabrous.

Leaves:

*Arrangement.*—Whorled with up to 5 leaves per node, opposite if only two leaves at one node.

*Length.*—10.0 cm to 12.0 cm.

*Width.*—4.0 cm to 4.5 cm.

*Shape.*—Lanceolate, curled.

*Margin.*—Serrate.

*Apex.*—Acuminate.

*Base.*—Shortly attenuate.

*Color.*—Upper surface: RHS 139A (Green). Lower surface: RHS 191A (Greyed-green) with RHS 185A (Greyed-purple) splotches.

*Texture.*—Dull; waxy.

*Variegation.*—Absent.

*Fragrance.*—Absent.

*Pubescence.*—Absent.

*Venation.*—Pinnate.

*Venation color.*—Upper surface: RHS 185C (Greyed-purple). Lower surface: RHS 185B (Greyed-purple).

*Petioles.*—Length: 0.5 cm to 1.0 cm. Diameter: 0.6 cm to 0.7 cm. Color: RHS 185C (Greyed-purple). Texture: Smooth, glaborous.

Flower buds:

*Shape.*—Deltoid, longitudinal cross-section.

*Length.*—1.5 cm to 2.0 cm.

*Diameter.*—1.5 cm.

*Color.*—RHS N74C (Red-purple) with RHS 185B (Greyed-purple) at the edge.

*Texture.*—Glabrous.

Inflorescence:

*Blooming habit.*—Will flower as long as the temperature is above 5° C.

*Inflorescence type.*—Single flower with spur.

*Number of flowers per node.*—1 to 3 in bloom at one time; about 10 to 12 flower buds.

*Number of flowers per plant.*—30 to 40.

*Lastingness of individual blooms on the plant.*—14 days.

*Fragrance.*—Absent.

Corolla:

*Shape.*—Roughly circular with 5 radial petals.

*Diameter.*—6.5 cm.

*Depth.*—0.1 cm to 0.3 cm.

Petals:

*Shape.*—Obcordate.

*Length.*—2.5 cm to 3.0 cm.

*Width.*—3.8 cm to 4.0 cm.

*Apex.*—Emarginate (cleaved).

*Base.*—Attenuate.

*Margin.*—Entire.

*Pubescence.*—Glabrous.

*Color.*—Upper surface: RHS N74B (Red-purple). Lower surface: RHS N74C (Red-purple) with RHS N74A vein between petal lobes. Eye zone: RHS N74A (Red-purple).

Spur:

*Shape.*—Tubular and curved downward.

*Color.*—RHS 186D (Greyed-purple).

*Length.*—4.8 cm to 5.0 cm.

*Diameter.*—0.2 cm to 0.3 cm.

Sepals:

*Shape.*—Lanceolate.

*Number.*—Two.

*Color.*—RHS 185D (Greyed-purple).

*Length.*—1.0 cm to 1.2 cm.

*Diameter.*—0.6 cm to 0.8 cm.

*Apex.*—Caudate.

*Base.*—Subcordate.

*Margin.*—Entire.

*Texture.*—Glabrous.

Reproductive organs:

*Stamens.*—Form: Fused; spill into 4 lobes. Number: Many. Filament length: 0.4 cm. Filament color: RHS N74B (Red-purple). Anther length: 0.5 cm. Anther color: RHS N155A (White). Pollen amount: Abundant. Pollen color: RHS N155A (White). Pollen description: Powdery.

*Pistil.*—Number: 5. Stigma color: RHS 139A (Green). Style color: RHS 139A (Green).

*Ovary arrangement.*—Parietal.

*Ovary surface color.*—RHS 1B (Green-yellow).

Fruit and seed set: No seed set observed.

Disease and insect resistance: No particular resistance or susceptibility has been observed.

COMPARISON WITH KNOWN CULTIVARS

'SAKIMP006' differs from the female parent, 'NG-02WM1', an unpatented *Impatiens* plant, in that 'SAKIMP006' has large, lavender flowers, while 'NG-02WM1' has medium, deep-orange flowers.

'SAKIMP006' differs from the male parent. 'NG-01H-9A', an unpatented proprietary *Impatiens* plant in that 'SAKIMP006' has lavender flowers, while 'NG-01H-9A' has red-orange flowers. Additionally, 'SAKIMP006' has a mounding growth habit, while 'NG-01H-9A' has an erect growth habit.

'SAKIMP006' is similar to the commercial *Impatiens* variety 'Misato FG3' (U.S. Plant Pat. No. 17,662) (known commercially as 'SunPatiens Magenta') however, there are differences as listed in the table below:

TABLE 1

Comparison of Characteristics between 'SAKIMP006' and 'Misato FG3'

| Characteristic | 'SAKIMP006' | 'Misato FG3' |
|---|---|---|
| Flower diameter | 6.5 cm | 6.0 cm |
| Petal color, Upper surface | RHS N74B (Red-purple) | RHS N66A (Red-purple) |
| Petal size (length and diameter) | Length: 2.5 cm to 3.0 cm<br>Diameter: 3.8 cm to 4.0 cm | Length: 2.4 cm to 3.0 cm<br>Diameter: 2.5 cm to 3.5 cm |

I claim:

1. A new and distinct cultivar of New Guinea *Impatiens* plant as shown and described herein.

* * * * *